(12) United States Patent
Wahl et al.

(10) Patent No.: US 7,799,192 B2
(45) Date of Patent: Sep. 21, 2010

(54) SENSOR ELEMENT

(75) Inventors: Thomas Wahl, Pforzheim (DE); Harald Guenschel, Gerach (DE); Berthold Ficker, Bamberg (DE)

(73) Assignee: Robert Bosch GmbH, Stuttgart (DE)

( * ) Notice: Subject to any disclaimer, the term of this patent is extended or adjusted under 35 U.S.C. 154(b) by 925 days.

(21) Appl. No.: 10/571,219

(22) PCT Filed: Aug. 11, 2004

(86) PCT No.: PCT/EP2004/051768

§ 371 (c)(1),
(2), (4) Date: Dec. 12, 2006

(87) PCT Pub. No.: WO2005/033691

PCT Pub. Date: Apr. 14, 2005

(65) Prior Publication Data

US 2007/0108049 A1 May 17, 2007

(30) Foreign Application Priority Data

Sep. 29, 2003 (DE) .............................. 103 45 141

(51) Int. Cl.
*G01N 27/26* (2006.01)
(52) U.S. Cl. .................... 204/424; 204/426; 204/429
(58) Field of Classification Search .............. 204/400, 204/410, 403.03, 408, 409, 421–429
See application file for complete search history.

(56) References Cited

U.S. PATENT DOCUMENTS 5,321,971 A 6/1994 Hobbs et al.
5,507,937 A * 4/1996 Renz et al. ................... 204/426
5,653,858 A * 8/1997 Friese et al. ................. 204/425
2003/0106796 A1* 6/2003 Emmei et al. ............... 204/426
2003/0116433 A1 6/2003 Diehl

FOREIGN PATENT DOCUMENTS

| DE | 198 17 012 | 12/1998 |
| JP | 60184400 | 9/1985 |
| JP | 7209246 | 8/1995 |
| JP | 11044670 | 2/1999 |
| JP | 2001153835 | 6/2001 |

* cited by examiner

*Primary Examiner*—Alexa D Neckel
*Assistant Examiner*—Jennifer Dieterle
(74) *Attorney, Agent, or Firm*—Kenyon & Kenyon LLP

(57) ABSTRACT

A sensor element to determine the temperature or the oxygen concentration of an exhaust gas of an internal combustion engine includes a first solid electrolyte film, a second solid electrolyte film, and a diffusion barrier disposed in a layer plane between the first and the second solid electrolyte film. A gas-impermeable or at least largely gas-impermeable cover layer is provided locally on the diffusion barrier, so that in the regions in which the cover layer is provided on the diffusion barrier, diffusion of the measured gas into or out of the diffusion barrier is at least largely prevented. A corresponding method for manufacturing a sensor element includes ablating a diffusion barrier using a laser in order to adjust the diffusion resistance of the diffusion barrier. A cover layer that, after a sintering process, is gas-impermeable or at least largely gas-impermeable is applied onto a side of the diffusion barrier that faces toward a measured gas located outside the sensor element. The cover layer is ablated in order to adjust the diffusion resistance of the diffusion barrier.

15 Claims, 5 Drawing Sheets

SENSOR ELEMENT

FIELD OF THE INVENTION

The invention relates to a sensor element and a method for manufacturing the sensor element.

BACKGROUND INFORMATION

A sensor element of this kind and a method for manufacturing the sensor element are described in published German patent document DE 198 17 012, which sensor element has, between a first and a second solid electrolyte film, an annular diffusion barrier that is surrounded by an annular measured gas space. Disposed in the measured gas space are electrodes to which a measured gas, located outside the sensor element, can travel via a gas entry opening installed in the first solid electrolyte film, and through the diffusion barrier.

Also known are sensor elements in which gas entry occurs through openings disposed in the layer plane between the first and the second solid electrolyte film.

In order to compensate for production-related fluctuations in the diffusion resistance of the diffusion barrier, the diameter of the gas entry hole and thus the inside diameter of the diffusion barrier are modified in controlled fashion. For this purpose, firstly a sensor element is sintered from a charge, and the so-called limit current (pumping current) of this sensor element is ascertained; the desired inside diameter of the diffusion barrier is ascertained on the basis of the measurement result, and the ascertained inside diameter is adjusted, by drilling, for the further sensor elements deriving from the same charge.

It is disadvantageous in this context that the method for ascertaining the limit current on the sintered sensor element, and the subsequent adaptation of the inside diameter of the diffusion barrier and the gas entry opening, are time-consuming and cost-intensive. It is additionally disadvantageous that even after the above-described correction of production-related fluctuations in the diffusion resistance, the limit current can vary because the magnitude of the diffusion barrier can be subject to a variation within a charge.

SUMMARY

The sensor element according to the present invention and the method for manufacturing the sensor element according to the present invention have the advantage that after sintering, the diffusion barrier can be processed with high accuracy in simple, time-saving, and economical fashion in order to compensate for production fluctuations in diffusion resistance related to production engineering.

For this purpose, the diffusion barrier that is disposed between a first and a second solid electrolyte film is coated, on its side facing toward the measured gas, with a cover layer. The cover layer is gas-impermeable or at least largely gas-impermeable. The diffusion barrier and/or the cover layer can thus be processed through a gas entry opening that is introduced into the first solid electrolyte film, and the diffusion resistance of the diffusion barrier can thereby be adjusted on the sintered element.

Also advantageous is a method in which the diffusion barrier inside the sintered sensor element is ablated using a laser. It is advantageous in this context that during ablation of the diffusion barrier using the laser, the diffusion resistance of the diffusion barrier can be measured by ascertaining the limit current of an electrochemical cell of the sensor element.

For purposes of this specification, a "largely gas-impermeable cover layer" is to be understood as a cover layer in which the quantity of measured gas flowing through the cover layer, or of a component of the measured gas flowing through the cover layer, corresponds to at most 10 percent of the quantity of the total measured gas flowing through the diffusion barrier, or of the total component of the measured gas flowing through the diffusion barrier.

The cover layer has an orifice through which the measured gas can travel via the diffusion barrier to the electrode, the orifice being disposed, in the context of a cylindrical or hollow-cylindrical diffusion barrier, centeredly on the diffusion barrier, for example as a circular orifice whose center point lies on the axis of symmetry of the diffusion barrier. This ensures that the diffusion path of the measured gas is substantially the same to all regions of the electrode. It is furthermore advantageous if the surface of the diffusion barrier covered by the cover layer is disposed parallel to a layer plane of the sensor element, and if an orifice (gas entry opening) is provided in the first solid electrolyte film, the cover layer being disposed on the side of the diffusion barrier adjoining the gas entry opening.

The gas entry opening is cylindrical in shape, and the diffusion barrier hollow-cylindrical. The cover layer is configured annularly and has a circular orifice. The respective center points and center axes are superimposed on one another. Diameter $d_1$ of the gas entry opening, inside diameter $d_2$ of the diffusion barrier, outside diameter $d_3$ of the diffusion barrier, and diameter $d_4$ of the circular orifices advantageously satisfy the condition $d_4<d_1<d_3$. Particularly advantageously, $d_1$ is in the range from 0.6 mm to 1.8 mm, and/or $d_2$ is in the range from 0.2 mm to 0.6 mm, and/or $d_3$ is in the range from 1.8 mm to 3.0 mm, and/or $d_4$ is in the range from 0.2 mm to 0.6 mm.

In an example embodiment, the condition $d_2 \leq d_4 < d_1$ is satisfied. In this embodiment, gas entry occurs both via the inside radius of the diffusion barrier and via that region of the diffusion barrier not covered by the cover layer. As a result, a portion of the exhaust gas has a shorter diffusion distance, and the diffusion flow through the diffusion barrier is increased.

In a further example embodiment, $d_4 \leq d_2$, so that the cover layer projects beyond the inside radius of the diffusion barrier and thus protects the diffusion barrier from deposition of damaging constituents of the exhaust gas. The layer thickness of the cover layer is at least as great as the layer thickness of the diffusion barrier, thus ensuring the mechanical stability of the projecting region of the cover layer.

As an alternative to the hollow-cylindrical geometry, a linear geometry can also be provided for the gas entry opening, diffusion barrier, and measured gas space; with this geometry the diffusion barrier and measured gas space are disposed one behind another and have approximately the same width and (including the cover layer) the same height. The gas entry opening is introduced, for example, as a gap into the first solid electrolyte film, the width of the gap corresponding to the width of the diffusion barrier.

In an alternative example embodiment, a further diffusion barrier is disposed between the cover layer and the first solid electrolyte film. The measured gas, or a component of the measured gas, can thus travel to the electrodes via the orifice in the cover layer and via the diffusion barrier, or directly via the further diffusion barrier. The measured gas diffusing through the further diffusion barrier does not flow through the orifice in the cover layer. The diffusion resistance is thus made up of one component of the further diffusion barrier and one component of the orifice in the cover layer and the diffusion barrier. Division of the diffusion flow into two branches simplifies equalization of the diffusion resistance, since the entire diffusion flow does not pass through the orifice in the cover layer. Advantageously, the inside diameter of the further diffusion barrier is larger than the inside diameter of the gas entry opening.

The diffusion barrier is ablated through the gas entry opening using a laser. Prior to ablation, the gas entry opening is also filled at least locally with the diffusion barrier. This simplifies accessibility for the laser, and increases the volume that can be ablated with the laser.

In an alternative example method for equalizing the diffusion resistance of the diffusion barrier, the cover layer and/or the diffusion barrier are ablated, using a laser, through the gas entry opening. Ablation is accomplished on the sintered sensor element, i.e., after the sintering process.

The limit current is ascertained during ablation of the diffusion barrier, and ablation is monitored on the basis of the ascertained limit current. This is done by applying a voltage to an electrochemical cell of the sensor element, one of the electrodes of the electrochemical cell being disposed behind the diffusion barrier in the diffusion direction. The voltage is sufficiently high that all the oxygen flowing through the diffusion barrier is pumped off by the electrochemical cell from the electrode located behind the diffusion barrier. Ablation is continued until a target value for the limit current is reached. The limit current measurement can also occur before and/or after ablation of the diffusion barrier, or ablation can be interrupted during determination of the limit current.

The eroded material resulting from ablation of the diffusion barrier is removed using a gas flow that is directed through an injection nozzle onto the diffusion barrier or onto the corresponding region of the diffusion barrier. In order not to distort the limit current that is to be determined, the gas flow has a defined oxygen partial pressure, e.g., the oxygen partial pressure of air, and is heated to a temperature of approximately 750 degrees Celsius.

DETAILED DESCRIPTION

Figure 1:
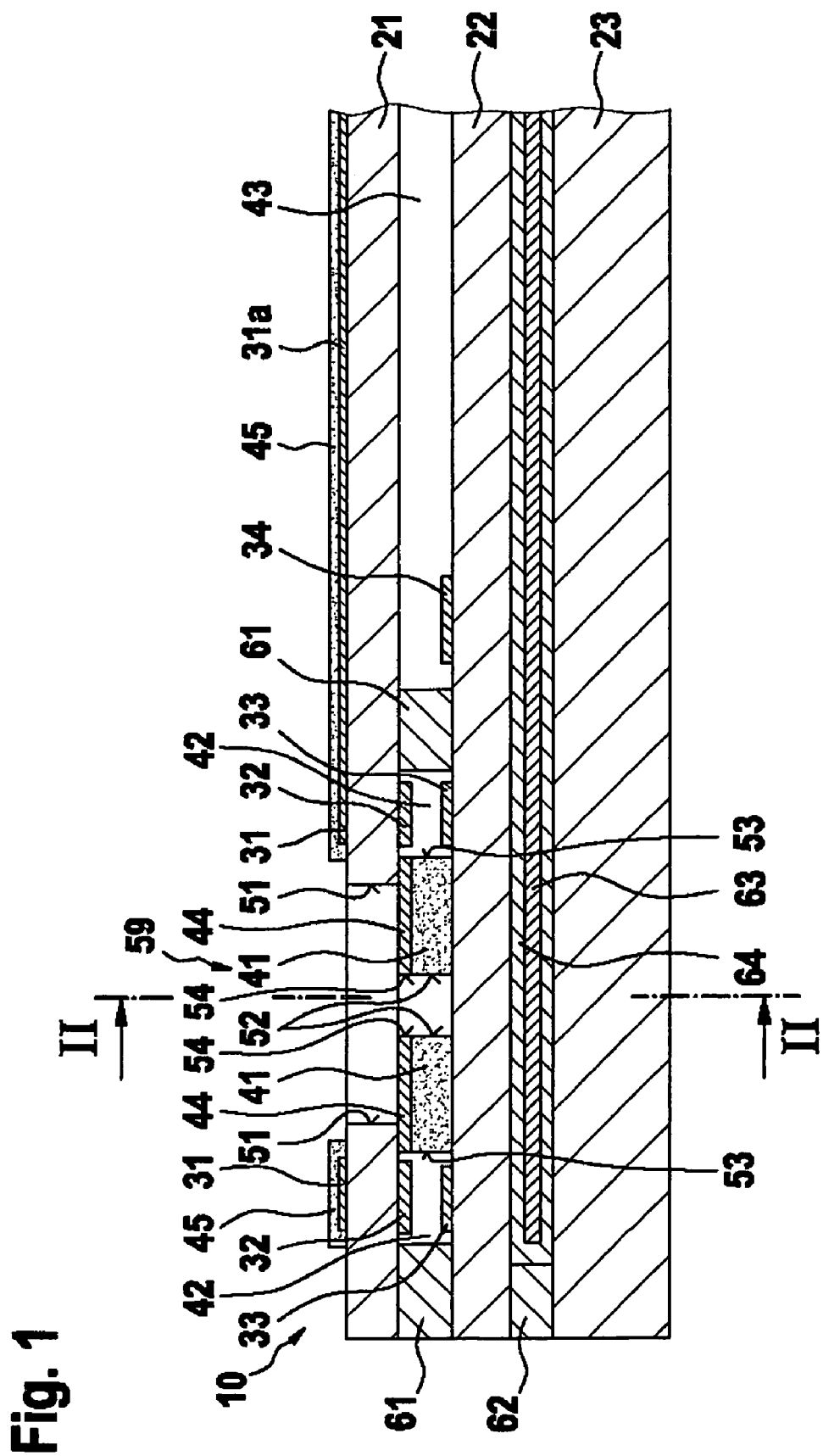
FIG. 1 shows a longitudinal cross-section through a first exemplary embodiment of the invention.
Figure 2:
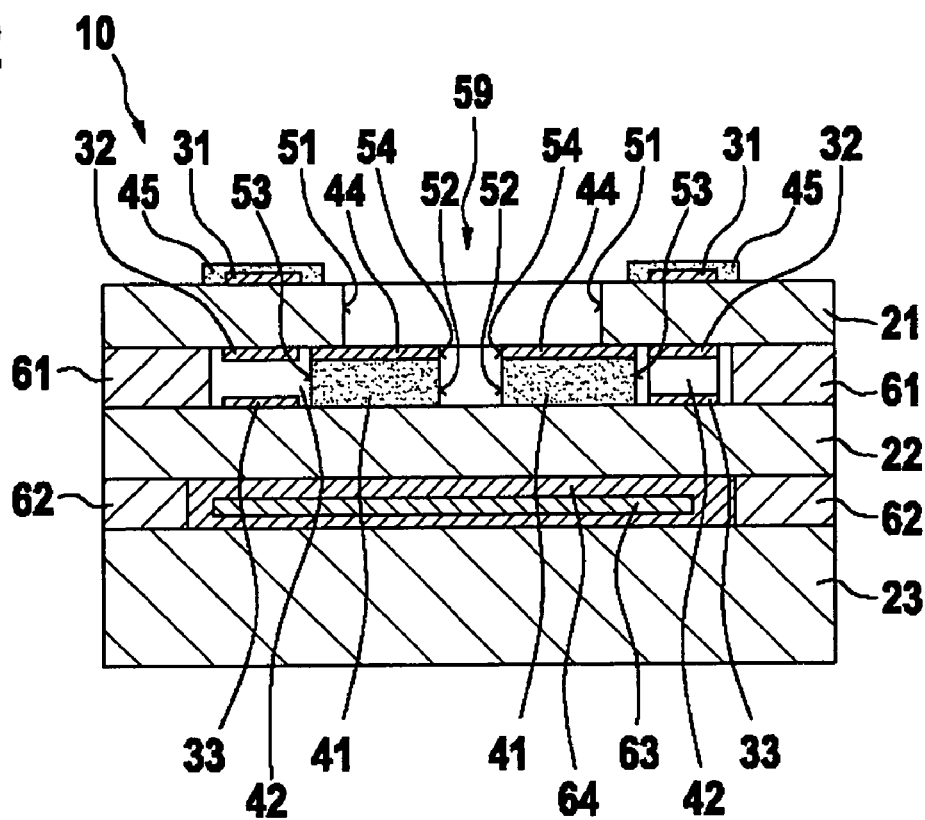
FIG. 2 shows a section, taken along line II-II in FIG. 1, through the first exemplary embodiment of the invention.

FIGS. 1 and 2 show a first exemplary embodiment of the invention having a sensor element 10 including a first, a second, and a third solid electrolyte film 21, 22, 23. Disposed on the outer side of first solid electrolyte film 21 is an annular first electrode 31, adjoining which is a supply lead 31a to first electrode 31. First electrode 31 is covered with a porous protective layer 45.

Introduced into first solid electrolyte film 21, inside the opening of first electrode 31, is a gas entry opening 59 having a first enveloping surface 51 that possesses a diameter $d_1$.

A hollow-cylindrical diffusion barrier 41 is disposed between first and second solid electrolyte films 21, 22. Diffusion barrier 41 has an inner enveloping surface 52 having a diameter $d_2$, and an outer enveloping surface 53 having a diameter $d_3$. Outer enveloping surface 53 of diffusion barrier 41 is surrounded by a measured gas space 42 that is likewise hollow-cylindrical in shape.

Additionally disposed between first and second solid electrolyte films 21, 22 is a reference gas space 43 that extends, proceeding from measured gas space 42, in the longitudinal direction of sensor element 10 and is filled with a ceramic material of low porosity. A sealing frame 61 is disposed between measured gas space 42 and reference gas space 43. Sealing frame 61 completely surrounds measured gas space 42 and seals it off from the outside.

An annular second electrode 32 is disposed in measured gas space 42 on first solid electrolyte film 21. Opposite second electrode 32, an annular third electrode 33 is provided in measured gas space 42 on second solid electrolyte film 22. A fourth electrode 34 that is exposed to a reference gas is disposed in reference gas space 43. The reference gas space can also be constituted by the pores of a porously configured fourth electrode or its supply lead, or by a porous ceramic layer.

Provided between second and third solid electrolyte films 22, 23 is a heater 63 that is electrically insulated from the surrounding solid electrolyte films 22, 23 by a heater insulator 64. Heater 63 and heater insulator 64 are surrounded laterally by a heater sealing frame 62.

The measured gas present outside sensor element 10 can travel, via gas entry opening 59 and via inner enveloping surface 52 of diffusion barrier 41, into measured gas space 42 and thus to second and third electrodes 32, 33.

First and second electrodes 31, 32, and solid electrolyte 21 disposed between first and second electrodes 31, 32, constitute an electrochemical pumping cell with which oxygen is pumped into or out of measured gas space 42. The oxygen partial pressure is determined by an electrochemical Nernst cell that is constituted by third and fourth electrodes 33, 34 and by solid electrolyte 22 located between third and fourth electrodes 33, 34. Based on the signal of the Nernst cell, the voltage applied to the pumping cell is controlled, by a control unit disposed outside the sensor element, in such a way that an oxygen partial pressure of lambda=1 is present in measured gas space 42. The oxygen partial pressure of the measured gas can be ascertained from the magnitude of the pumping current of the pumping cell.

The voltage applied to the pumping cell is selected to be sufficiently high that all the oxygen present in measured gas space 42 is pumped off. The pumping current is thus limited by the quantity of oxygen flowing through diffusion barrier 41. The pumping current flowing in this context constitutes the so-called limit current.

Production-related (e.g., geometric) fluctuations in diffusion barrier 41 can cause changes in, for example, the diffusion distance inside diffusion barrier 41 or the magnitude of diffusion barrier 41. Under otherwise identical conditions, the oxygen flow through the diffusion barrier, and therefore the limit current, may fluctuate; in the case of an elongation of the diffusion distance, for example, the diffusion flow and thus the limit current are reduced. The ultimate consequence of this is a distortion of the measurement result. Diffusion barrier 41 is therefore, according to the present invention, adjusted to a uniform oxygen flow through the diffusion barrier under uniform external conditions (adjusting diffusion resistance to a predefined target value for the limit current).

For that purpose, the sintered sensor element 10 is heated by heater 63 to operating temperature (e.g., 750 degrees Celsius), and is exposed to a measured gas having a defined oxygen concentration (e.g., ambient air). The oxygen flowing into measured gas space 42 is pumped out by the pumping cell (from second electrode 32 to first electrode 31), and the corresponding limit current is measured. At the same time material is ablated from sensor element 10, thereby influencing the oxygen flow flowing through diffusion barrier 41. Material ablation is continued until a target value for the limit current, which value corresponds to a target value for the oxygen flow flowing through diffusion barrier 41, is achieved. Diffusion barrier 41 is configured in such a way that, taking into account the production-related fluctuations that are to be expected, the diffusion flow prior to material ablation is less than the target value for the limit current, so that the diffusion distance is decreased by the material ablation and the diffusion flow can thus be increased until the target value is reached.

Provision is made for this purpose, in the case of the first exemplary embodiment according to FIGS. 1 and 2, to select a larger diameter for gas entry opening 59 than for the inside diameter of diffusion barrier 41. Diffusion barrier 41 can thus be ablated with a laser through gas entry opening 59. In order to arrive a defined gas flow with identical diffusion distances, oxygen needs to enter diffusion barrier 41 at inner enveloping surface 52. Diffusion barrier 41 is therefore coated, on its side facing toward measured gas opening 59, with a gas-impermeable cover layer 44. The desired diffusion resistance can thus be adjusted by ablating cover layer 44 and diffusion barrier 41 using a laser. In order to adjust the diffusion resistance, an opening is therefore introduced with the laser into both diffusion barrier 41 and cover layer 44, so that inside diameters $d_4$ and $d_2$ of cover layer 45 and diffusion barrier 41 are approximately equal.

The first exemplary embodiment according to FIGS. 1 and 2 has the following dimensions:

$d_1$=1.0 mm $d_2$=0.4 mm $d_3$=2.0 mm $d_4$=0.4 mm.

It is conceivable for the inner opening (enveloping surface 52) of diffusion barrier 41 not to be shaped cylindrically, for example, because diffusion barrier 41 is less severely ablated on the side facing toward second solid electrolyte film 22. In that case the inside radius of cover layer 44 corresponds to the inside radius of diffusion radius 41 at least in the region of diffusion barrier 41 directly bordering cover layer 44.

Cover layer 44 can also extend in the region between diffusion barrier 41 and first solid electrolyte film 21 (outside the gas entry opening).

In the case of the exemplary embodiments depicted in the subsequent Figures, elements corresponding to those shown in FIGS. 1 and 2 are labeled with the same reference characters.

Figure 3:
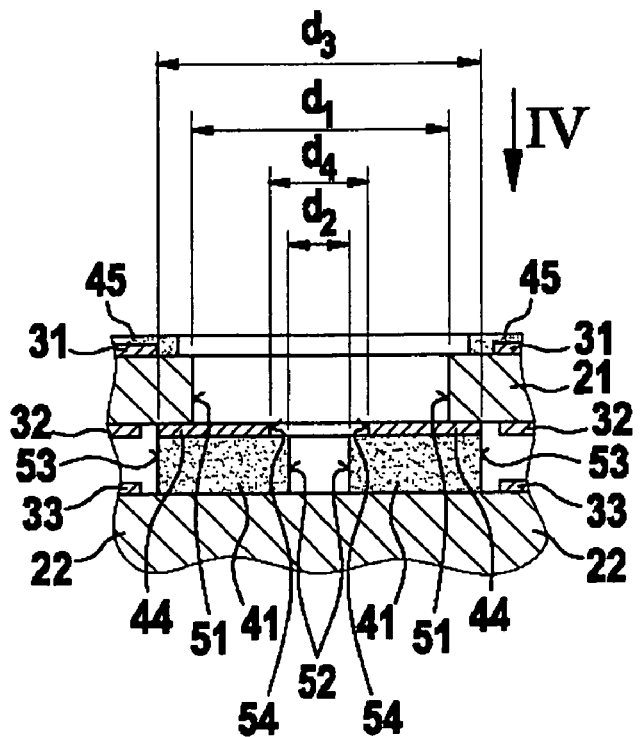
FIG. 3 shows a portion of a section through a second exemplary embodiment of the invention.
Figure 4:
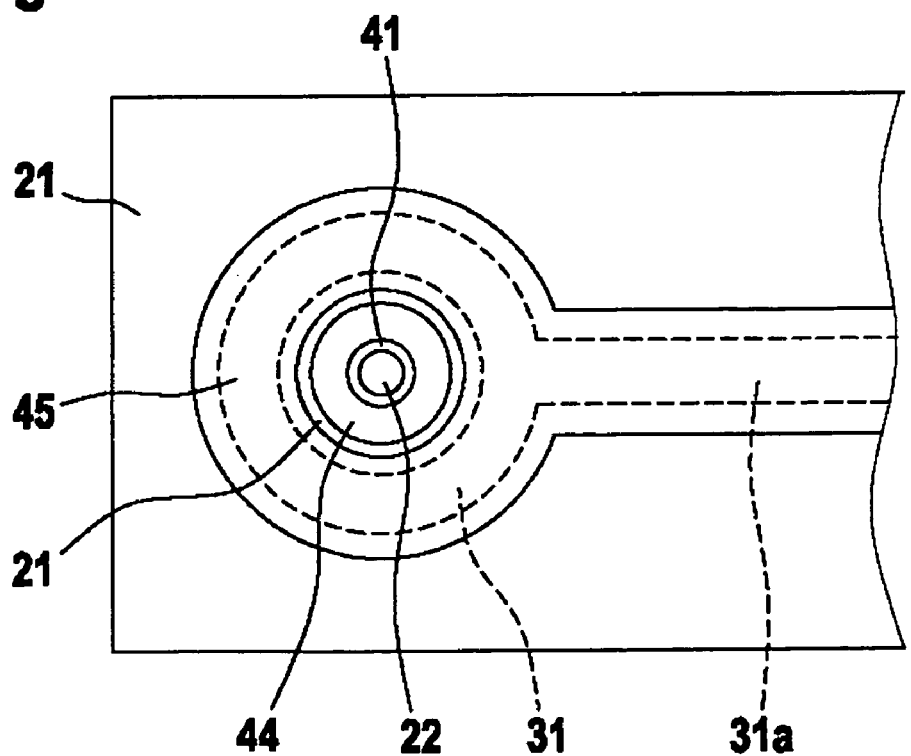
FIG. 4 is a plan view, in the direction IV indicated in FIG. 3, of the second embodiment of the invention.

FIG. 3 and FIG. 4 depict a second exemplary embodiment of the invention that differs from the first exemplary embodiment in terms of the configuration of cover layer 44. In the second exemplary embodiment, cover layer 44 has an inside radius $d_4$ that is larger than inside radius $d_2$ of diffusion barrier 41. In order to equalize the diffusion barrier, it is sufficient to ablate cover layer 44 in such a way that cover layer 44 has an opening 54 centeredly with respect to diffusion barrier 41. Largely similar diffusion distances to electrodes 32, 33 are achieved as a result of opening 54, centered with respect to diffusion barrier 41, in cover layer 44. In an alternative embodiment, diffusion barrier 41 may be cylindrical, i.e., has no opening 52.

The second exemplary embodiment according to FIGS. 3 and 4 has the following dimensions:

$d_1$=1.0 mm $d_2$=0.3 mm $d_3$=2.0 mm $d_4$=0.5 mm.

Figure 3A:
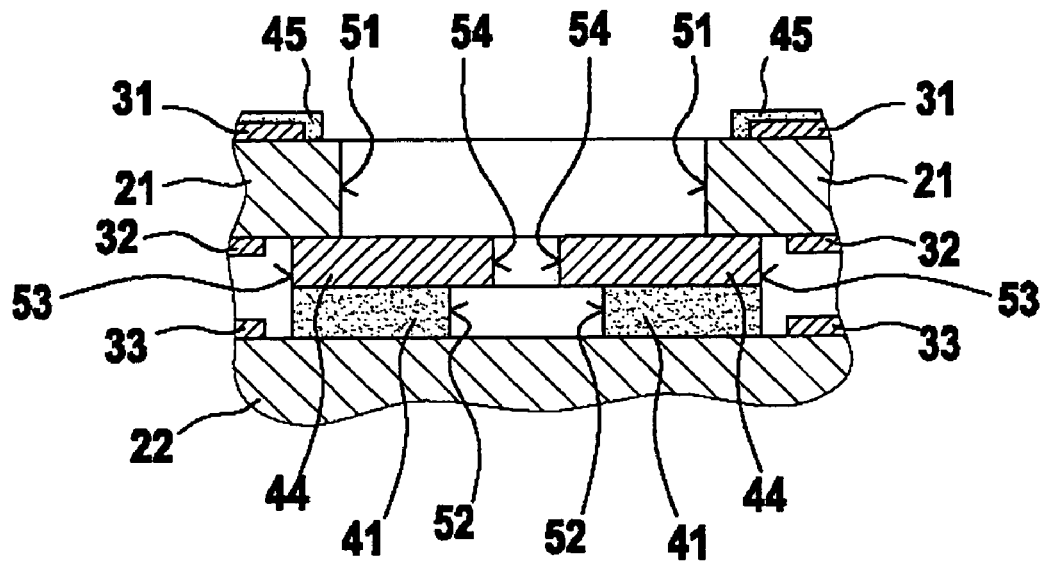
FIG. 3a shows a portion of a section through a further exemplary embodiment of the invention.

FIG. 3a depicts a further example embodiment of the invention in which inside diameter $d_4$ of cover layer 44 is smaller than inside diameter $d_2$ of diffusion barrier 41, so that cover layer 44 extends over the opening in diffusion barrier 41. A cavity paste is to be provided for that purpose in the opening in the diffusion barrier, which paste volatilizes upon sintering leaving no residue. The layer heights of cover layer 44 and of diffusion barrier 41 are identical in this embodiment, in order to ensure sufficient stability for the cover layer. The layer height of the cover layer is approximately 100 μm.

The embodiment according to FIG. 3a has the following dimensions:

$d_1$=1.0 mm $d_2$=0.5 mm $d_3$=2.0 mm $d_4$=0.3 mm.

Figure 5:
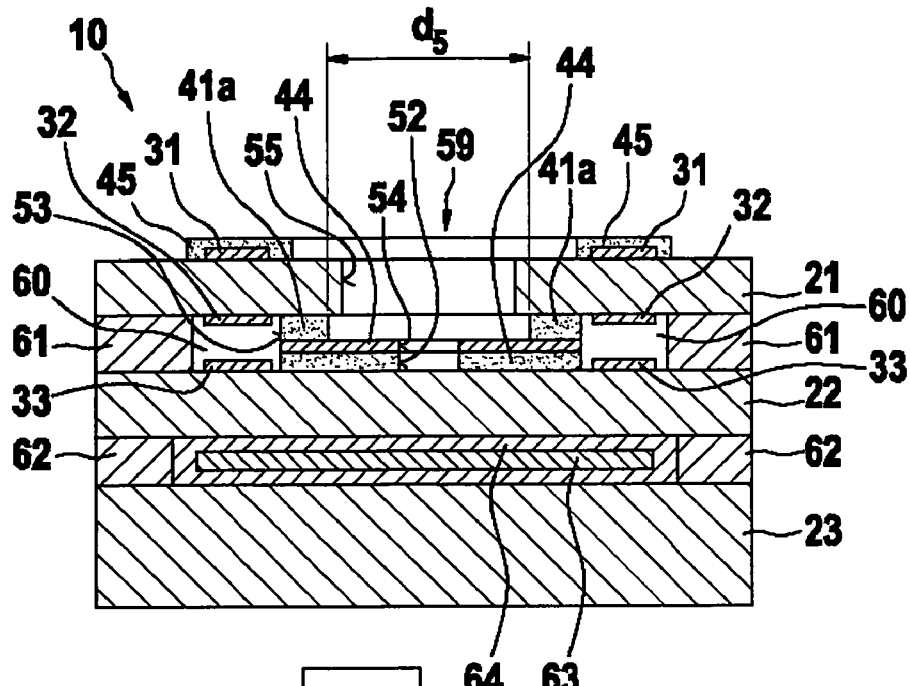
FIG. 5 shows a cross-sectional view of a third exemplary embodiment of the invention.

In the exemplary embodiment according to FIG. 5, a further hollow-cylindrical diffusion barrier 41a, having an inside radius $d_5$, is provided between cover layer 44 and first solid electrolyte film 21. The oxygen flow flowing into measured gas space 42 is thus divided into a portion that flows through further diffusion barrier 41a and a portion that flows through opening 54 in cover layer 44 and through diffusion barrier 41. In order to increase the equalization accuracy, diffusion barrier 41 and further diffusion barrier 41a are configured in such a way that the oxygen flow through further diffusion barrier 41a is greater than the oxygen flow through diffusion barrier 41. The portion of the oxygen flow through further diffusion barrier 41a amounts to 70 to 80 percent, and the portion of the oxygen flow through diffusion barrier 41 to 20 to 30 percent, of the total oxygen flow.

The inside diameter of further diffusion barrier 41a is equal to or greater than the inside diameter of gas entry opening 59. The ablation of cover layer 44, and (if applicable) of diffusion barrier 41, thus has no influence on the quantity of oxygen flowing through further diffusion barrier 41a. The outside diameters of diffusion barrier 41, of cover layer 44, and of further diffusion barrier 41a are approximately equal.

In an alternative embodiment, the cover layer may extend only as far as inner enveloping surface 55 of further diffusion barrier 41a.

Figure 6A:
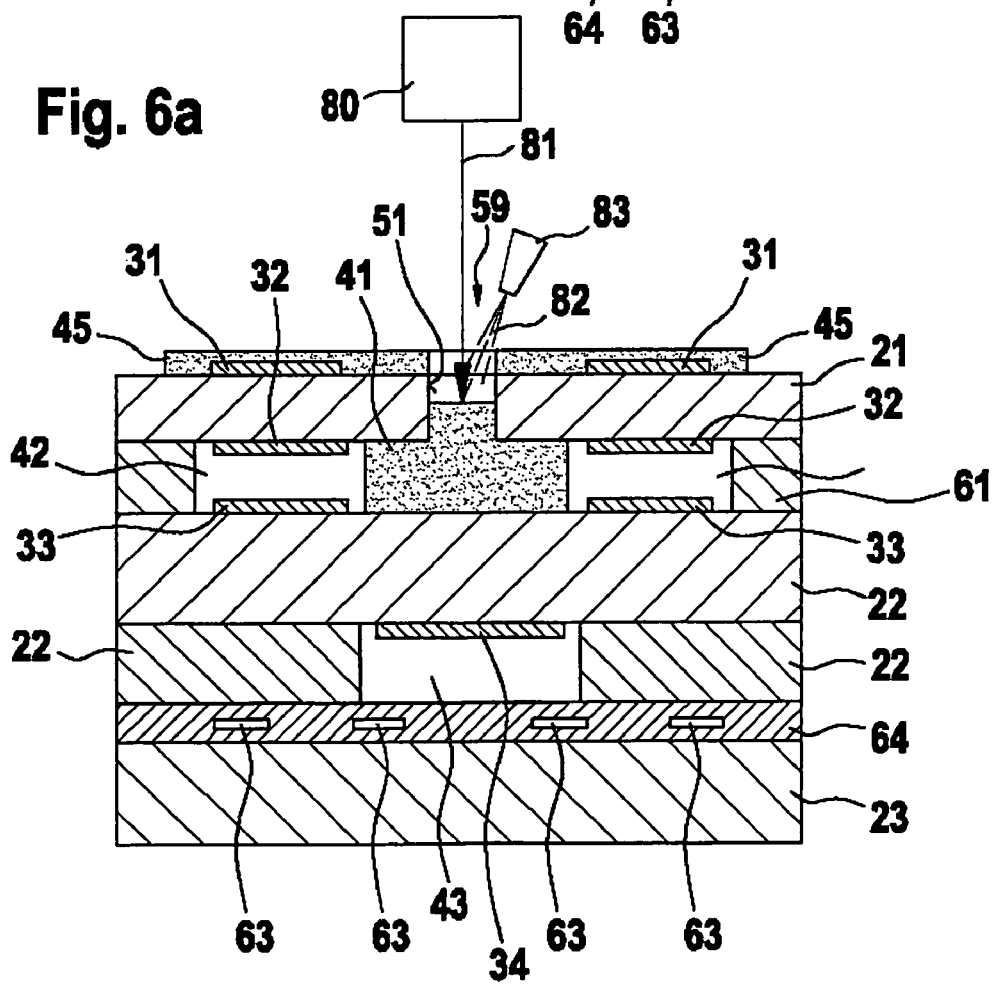
FIGS. 6a and 6b show a fourth exemplary embodiment of the invention before and after ablation of a region of the diffusion barrier using a laser.
Figure 6B:
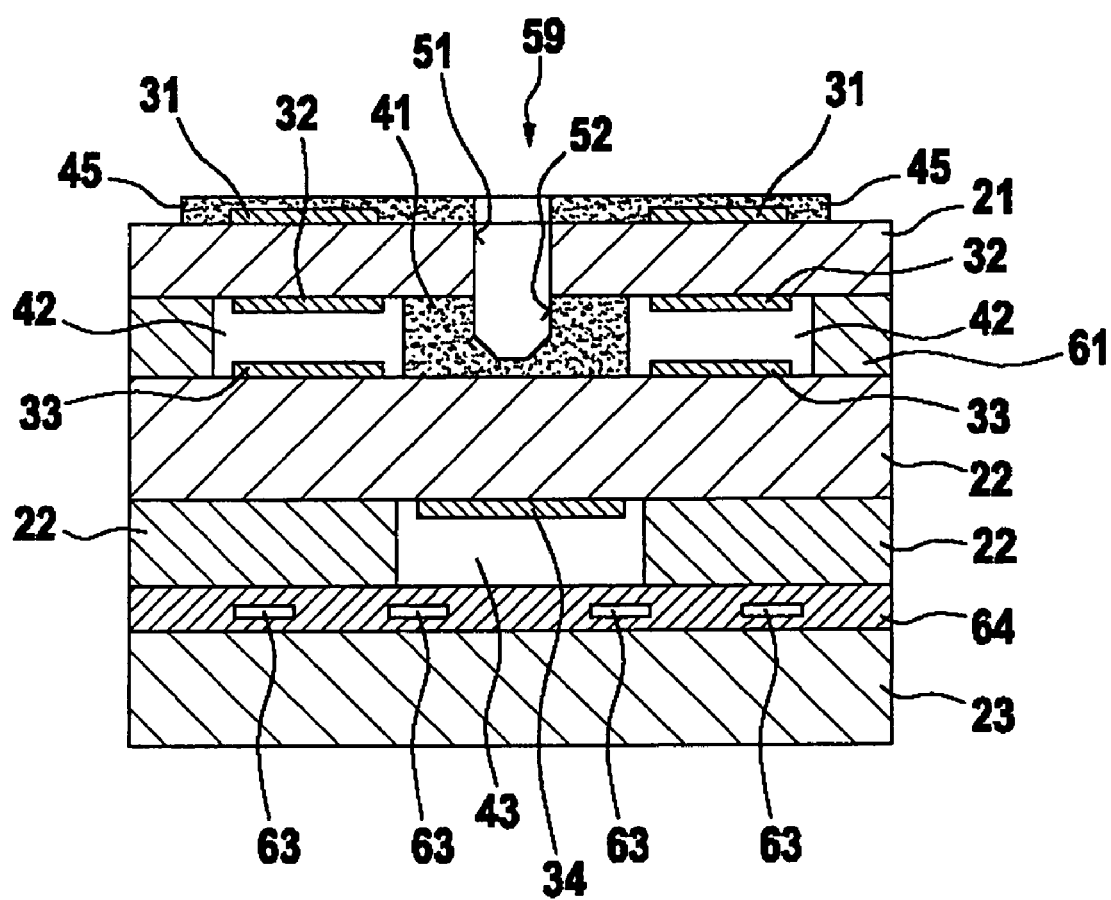

FIGS. 6a and 6b depict a method for adjusting the diffusion resistance in which a cover layer is omitted, and in which gas entry opening 59 is at least locally filled with diffusion barrier 41. After a sintering process, diffusion barrier 41 is ablated with a laser 81 while the limit current is continuously measured, until the target value for the limit current is reached.

In the method for adjusting diffusion resistance for the sensor elements according to FIGS. 1 to 6b, in general a laser beam 81 is directed, using an apparatus 80 for generating a laser beam 81, through gas entry opening 59 in first solid electrolyte film 21 onto cover layer 44 and/or diffusion barrier 41 of sintered sensor element 10 (see FIGS. 6a and 6b). In accordance with the method described above, material ablation is continued until the measured limit current corresponds to the predefined target value. The laser ablation of diffusion barrier 41 and/or of cover layer 44 produces eroded material. To remove the eroded material, an injection nozzle 83 is provided through which an air stream 82 (flushing gas) is directed onto diffusion barrier 41 and onto cover layer 44. The air stream, whose oxygen concentration corresponds to the oxygen concentration of the measured gas surrounding the sensor element, is heated to the operating temperature of the sensor element, for example to a temperature of 750 degrees Celsius, by a corresponding heating apparatus in injection nozzle 83.

In the exemplary embodiments described, the diffusion barriers, measured gas space, and gas entry opening exhibit a cylindrical geometry. The present invention applies equally to sensor elements in which diffusion into the measured gas space takes place linearly. For that purpose, the sensor element has an elongated conduit of largely constant width and height in which the diffusion barrier, and the measured gas space having the electrodes, are disposed (not depicted). A (for example) gap-shaped gas entry opening is provided in the first solid electrolyte film. The measured gas can travel through the gas entry opening and through the diffusion barrier into the measured gas space and to the electrodes. The diffusion direction of the measured gas is substantially parallel to the longitudinal axis of the sensor element. Provided on the diffusion barrier is the cover layer, which can be processed through the gas entry opening using a laser. The diffusion resistance is adjusted by ablating the cover layer and/or the diffusion barrier.

What is claimed is:

1. A sensor element for detecting a physical property of a measured gas, comprising:
    a first solid electrolyte film;
    a second solid electrolyte film;
    a diffusion barrier disposed in a layer plane between the first solid electrolyte film and the second solid electrolyte film;
    a gas-impermeable cover layer provided at least locally on the diffusion barrier so that in the regions in which the gas-impermeable cover layer is provided on the diffusion barrier, diffusion of the measured gas one of (a) into and (b) out of the diffusion barrier is substantially prevented; and
    a gas entry opening through the first solid electrolyte film provided to facilitate travel of the measured gas through the gas entry opening and the diffusion barrier to an internal electrode, wherein the gas-impermeable cover layer is provided on a side of the diffusion barrier facing toward the gas entry opening.

2. The sensor element as recited in claim 1, wherein the gas-impermeable cover layer is provided in a layer plane between the first solid electrolyte film and the diffusion barrier.

3. The sensor element as recited in claim 1, wherein the gas-impermeable cover layer is at least locally exposed directly to the measured gas, and wherein the gas-impermeable cover layer has an orifice through which one of the measured gas and a component of the measured gas travels via the diffusion barrier to the internal electrode.

4. The sensor element as recited in claim 3, wherein the orifice in the gas-impermeable cover layer is disposed substantially concentrically with respect to the diffusion barrier.

5. The sensor element as recited in claim 1, wherein the surface of the diffusion barrier covered by the gas-impermeable cover layer lies parallel to a layer plane of the sensor element.

6. The sensor element as recited in claim 1, wherein the gas entry opening is introduced into the first solid electrolyte film and has a first inside diameter d1, and wherein the diffusion barrier is configured in a substantially cylindrical shape having a second inside diameter d2 and a first outside diameter d3, and wherein the gas-impermeable cover layer has a circular orifice having a diameter d4.

7. The sensor element as recited in claim 6, wherein d4<d1<d3.

8. The sensor element as recited in claim 6, wherein at least one of: a) d1 is in the range of 0.6 mm to 1.8 mm; b) d2 is in the range of 0.2 mm to 0.6 mm; c) d3 is in the range of 1.8 mm to 3.0 mm; and d) d4 is in the range of 0.2 mm to 0.6 mm.

9. The sensor element as recited in one of claim 6, wherein d2≦d4.

10. The sensor element as recited in one of claim 6, wherein d4≦d2<d1.

11. The sensor element as recited in claim 6, wherein the gas entry opening, the diffusion barrier configured in a substantially cylindrical shape, and the circular orifice of the gas-impermeable cover layer are disposed concentrically with respect to each other.

12. The sensor element as recited in claim 1, further comprising:
    a further diffusion barrier disposed between the gas-impermeable cover layer and the first solid electrolyte film.

13. The sensor element as recited in claim 12, wherein the one of the measured gas and the component of the measured gas travels through the further diffusion barrier to the internal electrode without passing through an orifice provided in the gas-impermeable cover layer.

14. The sensor element as recited in claim 13, wherein the further diffusion barrier has an annular configuration and has an inside diameter d5, and wherein at least one of: a) d1≦d5; and b) d4≦d5.

15. The sensor element as recited in claim 14, wherein an outside diameter of the gas-impermeable cover layer is one of: a) larger than the inside diameter d5 of the further diffusion barrier; and b) substantially equal to the inside diameter d5 of the further diffusion barrier.

* * * * *